United States Patent [19]

Patel et al.

[11] Patent Number: 5,043,168

[45] Date of Patent: Aug. 27, 1991

[54] SOLID CHOLINE MAGNESIUM SALICYLATE COMPOSITION AND METHOD OF PREPARING SAME

[75] Inventors: Satishchandra P. Patel, Livingston; Vinayak T. Bhalani, Morris Plains, both of N.J.

[73] Assignee: Sidmak Laboratories, Inc., East Hanover, N.J.

[21] Appl. No.: 514,558

[22] Filed: Apr. 26, 1990

[51] Int. Cl.$^5$ .................. A61K 31/60; A61K 47/00
[52] U.S. Cl. .................. 424/682; 514/159; 514/790
[58] Field of Search .............. 424/682; 514/159, 770

[56] References Cited

U.S. PATENT DOCUMENTS

| | | |
|---|---|---|
| 173,607 | 2/1876 | Fehr . |
| 1,113,742 | 10/1914 | Bernedes et al. . |
| 1,486,373 | 3/1924 | Gerngross et al. . |
| 1,764,933 | 6/1930 | Coplans . |
| 1,845,486 | 2/1932 | Crossley . |
| 2,101,867 | 12/1937 | Miller et al. . |
| 2,801,951 | 8/1957 | Cooper, Jr. . |
| 2,970,163 | 1/1961 | Gottesman et al. . |
| 3,069,321 | 12/1962 | Broh-Kahn et al. . |
| 3,141,035 | 7/1964 | Lorz et al. . |
| 3,297,529 | 1/1967 | Berke . |
| 3,326,760 | 6/1967 | Halpern et al. . |
| 3,337,402 | 8/1967 | Zentner . |
| 3,759,980 | 9/1973 | Rosen et al. . |
| 3,801,613 | 4/1974 | Swimm . |
| 3,898,332 | 8/1975 | Swimm . |
| 3,947,491 | 3/1976 | Kelly et al. . |
| 3,965,263 | 6/1976 | Swimm . |
| 4,001,311 | 1/1977 | Kelly et al. . |
| 4,067,974 | 1/1978 | Sasmor . |
| 4,098,813 | 7/1978 | Kelly et al. . |
| 4,147,776 | 4/1979 | Kelly et al. . |
| 4,338,311 | 7/1982 | Heasley . |
| 4,761,274 | 8/1988 | Benick, Jr. et al. . |

FOREIGN PATENT DOCUMENTS 708865 5/1954 United Kingdom .

OTHER PUBLICATIONS

McGinity et al., "Increasing Dissolution Rates of Poorly Soluble Drugs by adsorption to Montmorillonite", *Drug Develop. and Industrial Pharmacy* 6(1), 35-48 (1980).

McGinity et al., "Influence of a Montmorillonite Clay on the Properties of Griseofulvin Tablets", Drug Development and Industrial Pharmacy, 6(1), 49-50 (1980).

"Mechanism of Release", *Drug Development and Industrial Phamacy*, 8(6), 795-809(1982).

R. T. Vanderbilt Co., Inc. booklet on Veegum.

Wai et al., "Applications of the Montmorillonites in Tablet Making", *Journal of Pharmaceutical Sciences*, vol. 55, No. 11, Nov. 1966.

Wai et al., "Some Physicochemical Properties of the Montmorillonites", *Journal of Pharmaceutical Sciences*, vol. 55, No. 11, Nov. 1966.

Harris et al., "Optimization of Slow-Release Tablet Formulations Containing Montmorillomite I. Properties of Tablets", *Drug Development and Industrial Pharmacy* 6(4), 399-410 (1980).

Harris et al., "Optimization of Slow Release Tablet Formulations Containing Montmorillonite II. Factors Affecting Drug Release", *Drug Development and Industrial Pharmacy*, 8(6), 783-793 (1982).

Harris et al., "Optimization of Slow-Release Formulations Containing Montmorillomite III".

*Primary Examiner*—Shep K. Rose
*Attorney, Agent, or Firm*—Sandler, Greenblum & Bernstein

[57] ABSTRACT

A stable, solid choline magnesium salicylate inclusion complex composition which comprises choline salicylate, magnesium salicylate and magnesium aluminum silicate, and granulation method for preparing the solid inclusion complex composition utilizing liquid salicylate is provided. The invention is also directed to methods of administering the compositions of the invention to treat osteoarthritis, rheumatoid arthritis, and acute painful shoulder.

46 Claims, 8 Drawing Sheets

13C, 68 MHZ, 4.5 KHZ CPMAS

Fig-7
13C, 68 MHZ, 4.6 KHZ CPMAS

Fig-8

13C, 68 MHZ, 4.6 KHZ CPMAS

Fig-10

13C, 68 MHZ, 4.5 KHZ CPMAS

SOLID CHOLINE MAGNESIUM SALICYLATE COMPOSITION AND METHOD OF PREPARING SAME

BACKGROUND OF THE INVENTION

1. Field of the Invention

The present invention relates to stabilized forms of choline salicylate, and more particularly to a stable solid choline magnesium salicylate inclusion complex composition which is useful in preparing solid, non-deliquescent pharmaceutical compositions.

2. Description of the Prior Art

Choline salicylate is a well-known analgesic compound having desirable pharmacological and therapeutic properties, as described in U.S. Pat. Nos. 3,069,321 and 3,141,035. The compound, however, possesses an inherent limitation of being highly hygroscopic so that it has been difficult to prepare pharmaceutically acceptable solid dosage forms which are useful for oral administration in the course of choline salicylate therapy of humans and animals. Although crystalline choline salicylate, melting at about 50° C., is known, its hygroscopic properties are such that trace amounts of moisture are sufficient to reduce the crystalline compound to the liquid state and no matter how stringent the effort to remove the absorbed moisture, the product remains in liquid state so that it cannot be used in forming stable solid dosage forms for pharmaceutical use.

The inherent limitations associated with liquid oral dosage forms presents well-known complications in the handling and dispensing of choline salicylate. Liquid preparations require more expensive packaging and special handling since breakage and spillage during shipment are quite common. Another limitation of liquid dosage forms is their difficulty in achieving a palatable, pleasing taste to mask the inherent noxious fishy taste and odor characteristic of choline compounds without use of additional taste masking components.

Various efforts have been made to prepare solid pharmaceutical dosage forms of choline salicylate.

British Patent Specification 708,865 discloses that choline salts are hydroscopic and tend to deliquesce and discolor. These disadvantages are obviated by treating the choline salts with calcium or magnesium oxides or hydroxides, water-soluble calcium or magnesium salts, or difficultly water-soluble or water-insoluble salts of calcium or magnesium with acids which are weaker than the acid contained in the acid choline salt. Specific examples include calcium or magnesium oxides, hydroxides, carbonates, bicarbonates and chlorides of these metals.

U.S. Pat. No. 3,297,529 to BURKE discloses the formation of a loose complex containing choline salicylate and magnesium sulfate which complex may be granulated with conventional excipients and pressed into tablets or encapsulated in gelatin or the like.

In contrast to BURKE, U.S. Pat. No. 3,326,760 to HALPERN discloses converting choline salicylate to a solid compound by reacting with polygalacturonic acid in aqueous alcoholic or hydroalcoholic medium. The resulting solid compound may then be mixed with a granulating aid and a tablet lubricant such as magnesium stearate and formed into tablets.

U.S. Pat. No. 3,759,980 to ROSEN et al. discloses salicylate compounds containing magnesium cation, choline cation and at least one anion selected from salicylic acid anion and acetylsalicylic acid anion. The generic formula of the disclosed compounds consists essentially of the following components:

$(R_1, R_2, R_3, R_4, N^+)_n (Mg^{++})_{n1} (ArCOO^-)_{n2}$
$(ArCOO^-)_{n3} (X^-)_{n4} (H_2O)_{n5}$ wherein $R_1$, $R_2$, $R_3$ and $R_4$ are selected from the group consisting of hydrogen, alkyl of 1 to 20 carbon atoms, hydroxyalkyl of 1 to 20 carbon atoms, carboxyalkyl of 1 to 20 carbon atoms and aralkyl of 1 to 20 carbon atoms in the alkyl moiety; Ar and Ar' are an aromatic monocycle or substituted aromatic monocycle; X is sulfate, chloride or substituted carboxylate; n, $n^1$ and $n^2$ are integers of at least 1 and $n^3$, $n^4$, and $n^5$ are 0 or an integer of at least 1, provided that when $(R_1, R_2, R_3, R_4, N^-)_n$ is choline, $(Mg^{++})_{n1}$ is magnesium, $(ArCOO^-)_{n2}$ is salicylate and $n^3$ is 0, and $(X^-)_{n4}$ is not sulfate. The compounds of ROSEN et al. are produced by mixing an aqueous solution of salicylate, such as choline salicylate, with an aqueous solution of a magnesium salt. Alternatively, ROSEN et al. disclose that a magnesium salt may be added as a solid to an aqueous salicylate solution, and the mixture agitated until the magnesium salt is dissolved to produce a homogeneous solution. According to either disclosed method, the resulting solution is evaporated to the degree of dryness desired, normally 2 to 4% by weight, so that a solid non-deliquescent complex may be obtained and powdered in a mill to the desired particle size.

U.S. Pat. Nos. 3,801,613 and 3,898,332 to SWIMM disclose choline salicylate trimethylsilyl-silicon dioxide compositions and uses thereof. The compound prepared in accordance with these patents is formed when choline salicylate is combined with silanized silicon dioxide under anhydrous conditions. A preferred method of preparing the choline salicylate-silanized silicon dioxide compound involves employing equimolar concentrations of choline chloride and sodium salicylate, suspending the mixture in acetone, mixing and then refluxing for approximately four hours. After cooling and filtering, silanized silicon dioxide, equivalent in weight to the amount of choline salicylate formed, is added to the filtrate and stirred. Subsequently, an equal volume of petroleum ether is added, and the mixture is allowed to stand overnight. Upon removal of the solvent, the formed choline salicylate-silanized silicon dioxide is dried at room temperature under low vacuum until it is free of solvent.

U.S. Pat. No. 3,947,491 KELLY deceased, et al. discloses choline salicylate sulfite and choline salicylate alkali metal sulfite-containing compounds. The disclosed choline salicylate salt-sulfite-complex compound is said to consist of, for example, choline salicylate sodium sulfite, choline salicylate potassium sulfite, or choline salicylate lithium sulfite. The method of preparation involves adding a sulfite-containing compound selected from the group consisting of sodium sulfite, potassium sulfite, and lithium sulfite to an equimolecular quantity of choline salicylate; mixing the same; allowing to stand for at least one-half hour; and recovering the formed choline salicylate salt-sulfite-complex compound.

SWIMM, U.S. Pat. No. 3,965,263, is directed to a method of achieving analgesia in an animal or a human comprising administering to the animal or human a therapeutically sufficient quantity of choline salicylate trimethylsilysilicon-dioxide. The patent also discloses a solid pharmaceutical composition for administering a salicylate-containing compound to an animal or human comprising an amount of 218 mg to 875 mg of choline salicylate trimethylsilysilicon-dioxide and a pharmaceutically acceptable carrier therefor.

KELLY, deceased et al., U.S. Pat. No. 4,001,311, is directed to a choline salicylate sulfite-containing compound selected from choline salicylate sodium bisulfite, choline salicylate sodium metabisulfite, choline salicylate sodium dithionate, choline salicylate sodium hydrosulfite, choline salicylate sodium hyposulfite, choline salicylate potassium bisulfite, choline salicylate potassium metabisulfite, choline salicylate potassium dithionate, choline salicylate potassium hydrosulfite, choline salicylate potassium hyposulfite, choline salicylate lithium bisulfite, choline salicylate lithium metabisulfite, choline salicylate lithium dithionate, choline salicylate lithium hydrosulfite and choline salicylate lithium hyposulfite.

SASMOR, U.S. Pat. No. 4,067,974, discloses the stabilization of choline salicylate in solid form by the addition of a metal salicylate having a valence of at least 2, preferably aluminum, bismuth, calcium or magnesium salicylate. The composition of SASMOR is said to be stabilized to a greater degree by the addition thereto of carboxymethylcellulose. SASMOR alleges that a still greater degree of stabilization is achieved by forming a complex of choline salicylate, metal salicylate and carboxymethylcellulose. This complex is prepared by forming a solution of carboxymethylcellulose, choline salicylate and metal salicylate, allowing the complexing reaction to take place, and subsequently drying.

KELLY, deceased et al., U.S. Pat. No. 4,098,813, is directed to a method for preparing a choline salicylate salt complex compound selected from the group consisting of choline salicylate sodium, potassium and lithium salts of bisulfite, metabisulfite, dithionate, hydrosulfite and hyposulfite. The method involves adding a sulfite containing compound to an equimolecular quantity of choline salicylate; mixing the same; allowing to stand for at least one-half hour and recovering the formed choline salicylate salt complex compound therefrom.

KELLY, deceased et al., U.S. Pat. No. 4,147,776, describes a method of suppressing color formation in a salicylate-containing pharmaceutical formulation which comprises adding between 0.1 to 5.0 percent by weight of a choline salicylate sulfite-containing compound to a salicylate-containing pharmaceutical dosage form, such as a syrup, tablet, gel, or eardrop form of choline salicylate.

HEASLEY, U.S. Pat. No. 4,338,311, discloses solid formulations of choline salicylate and hydrophilic silicon dioxide. The formulation preferably contains from about 35 to 45 parts by weight of hydrophilic silicon dioxide carrier. Formulations containing less than about 25 parts carrier are said to be undesirably hygroscopic and deliquescent. A suitable form of hydrophilic silicon dioxide for use with the disclosed composition includes hydrolyzed silica gel. A preferred method of preparation involves suspending a choline salt in an inert solvent; adding a metal salicylate salt; mixing; cooling the reaction mixture and filtering to remove the inorganic salt; adding an amount of hydrophilic silica to provide a proportion of hydrophilic silicon dioxide to choline salicylate within the specified range; evaporating the residual solvent; and drying the recovered choline salicylate hydrophilic silica formulation.

Despite the foregoing efforts to provide stable, solid formulations of choline salicylate for therapeutic use it appears that no completely satisfactory means for preparing a stable, solid choline salicylate complex is presently available in the art.

Besides the foregoing techniques for preparing solid compositions by reacting liquid choline salicylate with various materials, other procedures have been used to adsorb drugs to enable their delivery in solid dosage forms. While numerous adsorbates have been disclosed, U.S. Pat. No. 3,337,402 to ZENTNER discloses using Veegum to mask the bitter taste of 7-chloro-1-methyl-5-phenyl-3H-1,4-benzodiazepin-2(1H)-one. ZENTNER discloses on column 3, at lines 28 to 44, that 50 to 80 parts by weight of the Veegum (a trademark of R. T. Vanderbelt company for a complex of magnesium aluminum silicate) for each part of drug is preferred to adsorb this drug. In contrast, U.S. Pat. No. 4,761,274 to DENICK et al., discloses the use of magnesium aluminum silicates to adsorb various drugs. The disclosed process involves dissolving the medicament drug in a suitable solvent which is then permitted to sorb into the complex with mixing.

SUMMARY OF THE INVENTION

Generally, the present invention provides a stable, solid choline magnesium salicylate composition in the form of an inclusion complex comprising three essential components; namely, choline salicylate, magnesium salicylate and magnesium aluminum silicate. In the absence of any one of these three essential components from the formulations of this invention, unstable compositions are prepared.

In a preferred embodiment, the components of the choline magnesium salicylate composition are present in amounts such that the molar ratio of salicylate anion to choline cation and magnesium cation is about 7.2 to 2.4 and 6.0. This composition may optionally include pharmaceutically acceptable agents selected from the group consisting of fillers as extenders, colorants, flavorants, non-reactive buffers, preservatives, tableting excipients and mixtures thereof.

In another embodiment of the invention, the solid choline magnesium salicylate composition includes an amount of water of about 3.5 to about 10% by weight. This second composition may also contain pharmaceutically acceptable agents selected from the group consisting of fillers or extenders, colorants, flavorants, non-reactive buffers, preservatives, tableting excipients and mixtures thereof.

The present invention also contemplates a method for preparing a stable, solid choline magnesium salicylate composition, which comprises:

(a) providing a dry mixture comprising magnesium salicylate and magnesium aluminum silicate;

(b) granulating said mixture with liquid choline salicylate to form a granulated choline magnesium salicylate inclusion complex containing magnesium aluminum silicate; and (c) recovering said solid choline magnesium salicylate inclusion complex composition.

In a preferred method of preparation, the mixture of step (a) further includes a pharmaceutically acceptable agent selected from the group consisting of silicon dioxide, sodium starch glycolate, and mixtures thereof.

In another preferred method of preparation, the mixture of step (a) is blended to provide a homogeneous mixture prior to granulation step (b).

Preferably, drying is performed after granulation which comprises drying the liquid choline magnesium salicylate inclusion complex at a temperature of from about 28° C. to about 60° C. for not less than about twelve hours.

According to another aspect of the present invention, a method of treating osteoarthritis in a mammal is provided, such as a human or animal, the method which comprises administering to said mammal a therapeutically effective quantity of a solid choline magnesium salicylate inclusion complex comprising choline salicylate, magnesium salicylate and magnesium aluminum silicate.

According to another aspect of the invention, a method of treating rheumatoid arthritis in a mammal is provided, such as a human or animal, the method which comprises administering to said mammal a therapeutically effective quantity of a solid choline magnesium salicylate inclusion complex comprising choline salicylate, magnesium salicylate and magnesium aluminum silicate.

According to another aspect of the invention, a method of treating acute painful shoulder in a mammal is provided, such as a human or animal, the method which comprises administering to said mammal a therapeutically effective quantity of a solid choline magnesium salicylate inclusion complex comprising choline salicylate and a matrix comprising magnesium salicylate and magnesium aluminum silicate.

The present invention also contemplates a method of administering a solid choline magnesium salicylate pharmaceutical preparation to a mammal, the method which comprises providing the solid choline magnesium salicylate composition comprising an inclusion complex of choline salicylate, magnesium salicylate, and magnesium aluminum silicate; incorporating said inclusion complex into a pharmaceutically acceptable carrier to form a solid choline magnesium salicylate preparation, and delivering said solid choline magnesium salicylate preparation to a mammal. Suitable pharmaceutically acceptable carriers for the formulations of the invention include tablets, capsules, granules, and suppositories.

DETAILED DESCRIPTION OF THE INVENTION

Applicants have unexpectedly discovered a stable, solid choline magnesium salicylate composition comprising an inclusion complex of choline salicylate, magnesium salicylate and magnesium aluminum silicate. The invention therefore requires the essential presence of three components in the inclusion complex: choline salicylate, magnesium salicylate, and magnesium aluminum silicate, in order to prepare the solid, stabilized formulations of the invention.

The solid choline magnesium salicylate composition of the invention may be substantially anhydrous or may contain a certain amount of water. The water, optionally present in the formulations of the invention, may be bound or unbound. The term substantially anhydrous refers to formulations which are dried and contain up to about 10% by weight water, and preferably from about 4 to 6% water by weight of the total formulation. The inclusion complex is capable of absorbing moisture from the atmosphere without losing its solid free-flowing properties. In this regard, moisture increases of at least from 1 to 12% have been found to occur without any change in the solid form of the final product.

The first essential component of the inventive formulations, namely choline salicylate, is a commercially available material having the formula $C_{12}H_{19}NO_4$. Choline salicylate is a non-steroidal anti-inflammatory that exhibits analgesic and antipyretic activity. An advantage of the present invention is the utilization of liquid choline salicylate to prepare the stabilized solid choline magnesium salicylate compositions of this invention without the need to dry the liquid choline salicylate prior to using it in the process of this invention.

Magnesium salicylate, $C_{14}H_{10}MgO_6$, is the second essential component of the composition of the invention. Magnesium salicylate is a commercially available agent which has been discovered to interact with choline salicylate and magnesium aluminum silicate to form an inclusion complex for stabilizing choline salicylate in solid form. Magnesium salicylate is preferably used as a solid free-flowing powder in the formulations of the invention.

Use of the phrase "choline magnesium salicylate" is meant to include salicylate containing formulations, such as choline magnesium trisalicylate, and hydrated inclusion complexes thereof which formulations contain a therapeutically effective amount of salicylate.

When the choline salicylate and magnesium salicylate components are present in the formulations of this invention, they are preferably present in amounts of about 65% to about 85% by weight of the total formulation. Such amounts have been found to be acceptable to provide the therapeutically effective amount when the formulation is tableted using conventional excipients. Each 500 mg tablet should contain about 293 mg of choline salicylate combined with about 362 mg of magnesium salicylate to provide 500 mg salicylate content. Each 750 mg tablet contains about 440 mg of choline salicylate combined with about 544 mg of magnesium salicylate to provide 750 mg salicylate content and each 1000 mg tablet contains about 587 mg of choline salicylate with about 725 mg magnesium salicylate to provide 1000 mg salicylate.

The third essential component of the formulations of the invention is magnesium aluminum silicate. Magnesium aluminum silicate, $Al_2MgO_8Si_2$, is a commercially available hydrophilic absorbing/binding agent which has been found to interact with choline salicylate and magnesium salicylate to form an inclusion complex or matrix which stabilizes the choline salicylate active component.

A particularly preferred form of magnesium aluminum silicate is identified as "Veegum" which has an average chemical analysis as follows: silicon dioxide 59.5%, magnesium oxide 13.0%, aluminum oxide 8.9%, ferric oxide 1.0%, calcium oxide 2.0%, sodium oxide 2.1%, potassium oxide 1.3% with an ignition loss of 11.1%. A particularly preferred grade of Veegum is Veegum F supplied by R. T. Vanderbilt Company. This grade is a microfine powder having a 325 mesh size (U.S. standard sieve size) and which has an aluminum to magnesium ratio of 0.5 to 1.2.

The term "inclusion complex" and "matrix" as utilized herein means complexes and partial complexes, formed by the ionic interaction of choline cations, magnesium cations, aluminum cations, silicate anions and salicylate anions resulting from use of choline salicylate, magnesium salicylate and magnesium aluminum silicate. The exact chemical nature of the inclusion complex formed by the interaction between the choline salicylate, magnesium salicylate and magnesium aluminum silicate is not known with certainty but it is believed that the nature of the complex varies depending upon the particular amounts of components present, the degree of water of hydration in the formulation, the granulation process for making the composition, etc. Preferred solid, stable inclusion complexes are formed when the magnesium aluminum silicate is employed in amounts of about 6% to about 35% and preferably about 8% to about 15% by weight, which provides stabilized solid choline magnesium salicylate compositions useful for solid dosage pharmaceutical applications. When amounts of less than about 6% magnesium aluminum silicate are used, an acceptable granulated product is not able to be prepared which is nondelinquescent is nature. Amounts above about 35% do not significantly enhance granulation and may alter the drug availability once tabletted.

The compositions of the present invention may include a wide variety of pharmaceutically acceptable additives well-known in the tableting art, including pharmaceutically acceptable agents selected from the group consisting of fillers, extenders, colorants, flavorants, non-reactive buffers, preservatives, tableting excipients and mixtures thereof.

The fillers and extenders useful in the invention include those materials normally useful in the pharmaceutical industry and include without limitation inert mineral powder such as calcium carbonate, silicates, soft clays, soybean extracts and so forth. A particularly preferred material is silicon dioxide.

When silicon dioxide is employed in the formulations of this invention, it is used along with the magnesium aluminum silicate and may even replace some of the magnesium aluminum silicate present in the formulation. When used in combination the combined amount of both ingredients is from about 15% to about 35% by weight of the total formulation. Additionally, the combination is used in a percent weight ratio of magnesium aluminum silicate to silicon dioxide of 70:30 to 30:70.

The fillers and/or extenders are used in amounts of about 6% to about 35% by weight and preferably in amounts of about 8% to about 15% by weight of the total formulation.

The colorants useful in the present invention include pigments such as titanium dioxide, and may also include dyes suitable for food, drug and cosmetic applications. These colorants are known as F.D. & C. dyes. A full recitation of F.D. & C and D. & C. colorants and their corresponding chemical structures may be found in the Kirk-Othmer Encyclopedia of Chemical Technology, 3rd Edition, in Volume 6, at pages 561-595.

Flavoring agents well-known in the pharmaceutical art may be added to the compositions of the instant invention. These flavoring agents may be chosen from synthetic flavor oils and/or oils derived from plants, leaves, flowers, fruits and so forth, and combinations thereof. Representative flavor oils include: spearmint oil, cinnamon oil, oil of wintergreen (methylsalicylate) and peppermint oils. Also useful are artificial, natural or synthetic fruit flavors such as citrus oil including lemon, orange, grape, lime and grapefruit, and fruit essences including apple, strawberry, cherry, pineapple and so forth. The flavoring agent may be solid, spray dried, encapsulated, adsorbed on a carrier and mixtures thereof.

Suitable non-reactive buffers include calcium, sodium and magnesium carbonates, phosphates, stearates, and citrates, all well known in the art. A preferred buffering agent utilized in accordance with the present invention is sodium starch glycolate. The buffer is employed in suitable amounts which may vary from about 1% to about 10% and preferably about 2% to about 6% by weight of the total formulation.

Preservatives which may be used in the pharmaceutical formulations of the invention include those known antimicrobial agents conventionally employed in the art, such as benzoic acid and sodium benzoate; the parabens; sorbic acid and salts thereof; propionic acid and salts thereof; acetic acid and salts thereof; nitrates and nitrites; sulfur dioxide and sulfites; antibiotics; diethyl pyrocarbonate; epoxides; hydrogen peroxide; and phosphates. The parabens include the methyl, ethyl, propyl, and butyl esters of parahydroxybenzoic acid.

The tableting excipients useful in the inventive formulations include those well known in the tableting industry such as talc, propylene glycol, wax powders, gum arabic and so forth.

In addition, once the tablets are prepared they may be coated with conventional coating agents, such as shellac, starch, cellulose derivatives and so forth.

In general, the stable, solid choline magnesium salicylate compositions of the present invention are prepared by a method which comprises:

(a) providing a dry mixture comprising magnesium salicylate and magnesium aluminum silicate;

(b) granulating said mixture with liquid choline salicylate to form a granulated choline magnesium salicylate inclusion complex; and (c) recovering a solid choline magnesium salicylate inclusion complex composition.

The mixture of step (a) is preferably preblended to provide a homogenous mixture prior to granulation. The inventive method advantageously utilizes means for blending solids and liquids well-known to those of ordinary skill in the art. The magnesium salicylate and magnesium aluminum silicate are preferably used as free-flowing solid particles and preblended simply by mixing the ingredients together.

When present, the preferred silicon dioxide filler and sodium starch glycolate buffer are preblended, as free-flowing powders, with the magnesium salicylate and magnesium aluminum silicate to form a homogeneous mixture prior to granulation with the liquid choline salicylate.

Granulation is performed in a conventional manner well known to the ordinary skilled artisan. Such procedures generally involve simply mixing the liquid choline salicylate with the preblend. The liquid choline salicylate may contain from 50 to 85% choline salicylate and the remainder water, and preferably contains 78 to 82% choline salicylate and most preferable 80%. Mixing may be achieved while the powder mix is added in incremental amounts to the liquid choline salicylate or preferably while the liquid choline salicylate is added in incremental amounts to the powder mixture while mixing is performed. While not necessary it may be advantageous to use additional amounts of water during the granulation process. Once all of the components have been added together, mixing is continued for from 1 to 60 minutes in order to prepare a homogenous granulated formulation. It has been found that mixing times of about 5 to 10 minutes are satisfactory for preparing acceptable formulations which are ready for storage or further processing to form a tableted product.

After granulation, the resulting composition is essentially dry to the touch and may be immediately stored or further processed to prepare the final tableted pharmaceutical formulations. Alternatively, the granulated composition may be optionally dried to remove excess water. When performed drying is preferably carried out at a temperature of from about 28° C. to about 60° C. for not less than approximately twelve hours and preferably at about 40° C. to about 50° C. Conventional drying apparatus known in the art may be employed.

The granulated formulation contains water in amounts from about 3.5% to about 10% by weight of the granulated composition. When dried the granulated formulation preferably contains from about 5% to about 8% water by weight. The water present in the formulation is present as water of hydration and free water. It has been unexpectedly discovered that the formulations of this invention possess a limited degree of hygroscopicity wherein the formulations are capable of adsorbing atmospheric moisture without changing from its solid, free-flowing form. This unusually and unexpected physical property is believed to occur from the presence of the magnesium aluminum silicate which is capable of expanding its intersticial spaces between the platelets which make up this structure when water is absorbed. Sorbtion appears to cause an enhanced ionic bonding between the respective components which strengthens the matrix or inclusion complex formed by the present formulation. While not being bound to any particular theory, it is believed that as granulation proceeds and the magnesium aluminum silicate and water from the liquid choline salicylate are mixed together, the water penetrates the area between the magnesium aluminum silicate platelets forcing them apart. As this occurs, exchangeable ions begin to diffuse away from the platelet faces and become complexed with the choline, magnesium and salicylate ions present in the active components. The resulting structure can be pictured as parallel platelets connected by perpendicular crosslinked platelets.

The compositions provided by the present invention may be employed as analgesic and antipyretic therapeutic agents to treat a variety of conditions such as osteoarthritis, rheumatoid arthritis, and acute painful shoulder.

Solid choline magnesium salicylate compositions provided by the present invention may be administered to a mammal such as an animal or human to treat the above-noted conditions by a method which comprises: providing a solid choline magnesium salicylate inclusion complex comprising choline salicylate, magnesium salicylate and magnesium aluminum silicate; incorporating said solid choline salicylate inclusion complex into a pharmaceutically acceptable carrier to form a solid choline magnesium salicylate pharmaceutical preparation; and delivering said solid choline magnesium salicylate pharmaceutical preparation to a mammal, such as an animal or human.

Preferred pharmaceutical carriers include those carriers suitable for solid therapeutic agents well-known in the art such as tablets, capsules, granules, and suppositories. The techniques for incorporating the solid choline magnesium salicylate compositions of the invention into such carriers are well-known to those skilled in the art and do not constitute a novel feature of the this invention. Solid tablet dosage forms may be optionally film-coated to provide an additional moisture barrier and improved aesthetic appearance of the final product.

The following examples are given to illustrate the invention, but are not deemed to be limiting thereof. All percentages given throughout the specification are based on the weight of the final core solid choline magnesium salicylate composition (that is the granulated solid product) unless otherwise indicated. All formulations result in compositions having 100% components contained therein.

EXAMPLE 1

Inventive Run 1

Preparation of a Solid Choline Magnesium Inclusion Complex

This example illustrates the preparation of a stable, solid choline magnesium salicylate composition suitable as a core composition in a choline magnesium salicylate tablet formulation.

The following components are utilized in the composition:

| Ingredient | Weight Percent |
|---|---|
| Choline Salicylate (80%) | 31.68 |
| Magnesium Salicylate | 39.14 |
| Magnesium Aluminum Silicate | 10.16 |
| Silicon Dioxide | 12.86 |
| Sodium Starch Glycolate | 4.00 |
| Talc | 1.08 |
| Magnesium Stearate | 1.08 |
| | 100.00 |

Solid free-flowing powders of magnesium salicylate, magnesium aluminum silicate, silicon dioxide, and about 60% of the sodium starch glycolate are placed into a mixer and blended for fifteen minutes. After a homogeneous mixture is obtained, the blend is granulated with liquid choline salicylate wherein the liquid is slowly added to the powder preblend. The mixture is continuously blended until completely granulated. The resulting granular mass is then transferred onto paperlined trays and dried in a tray drier at 40° C. to 50° C. for not less than about 12 hours. The dried mass is milled through a #12 mesh screen. Upon checking the amount of weight lost from drying, the mass is redried until the total weight is within the desired range of about 3.5% to about 8%. The dried mass, talc (screened through a #18 mesh screen), and the remainder of the sodium starch glycolate are then transferred into a ribbon blender and blended for about 15 minutes.

The blend is recycled and blended for 10 more minutes. The magnesium stearate is screened through a #18 mesh screen directly into the blender and the mixture is blended for an additional 5 minutes.

The resulting dry choline magnesium salicylate composition may then be compressed and formed into tablets by techniques well-known in the art, or stored for future use.

The composition is found to be stable and non-deliquescent, thereby providing a solid choline magnesium salicylate composition which resists degradation in the presence of water. The resulting water content of the formulation was about 5.3% by weight.

Figure 1:
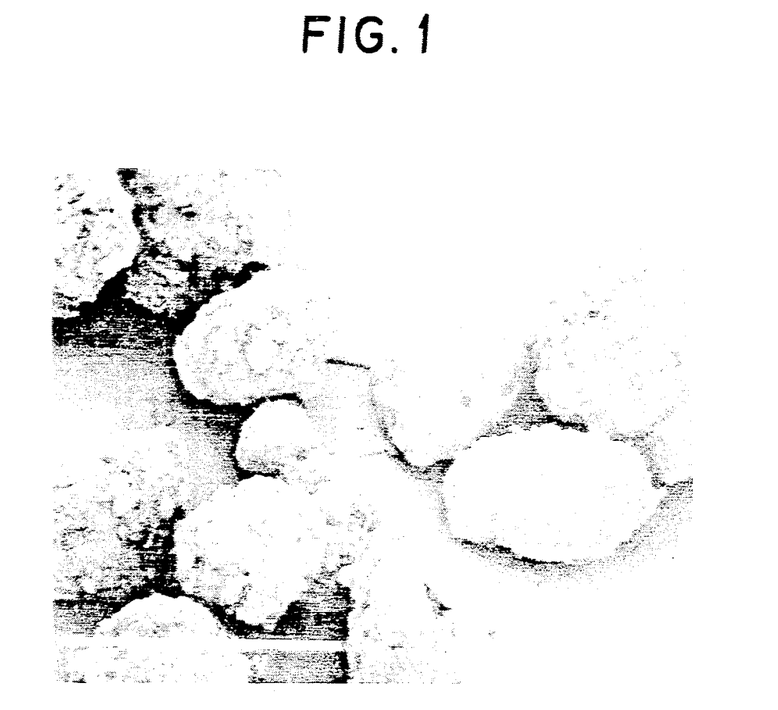
FIG. 1 is an electron micrograph of Example 4, Inventive Run 2 at 50X.
Figure 2:
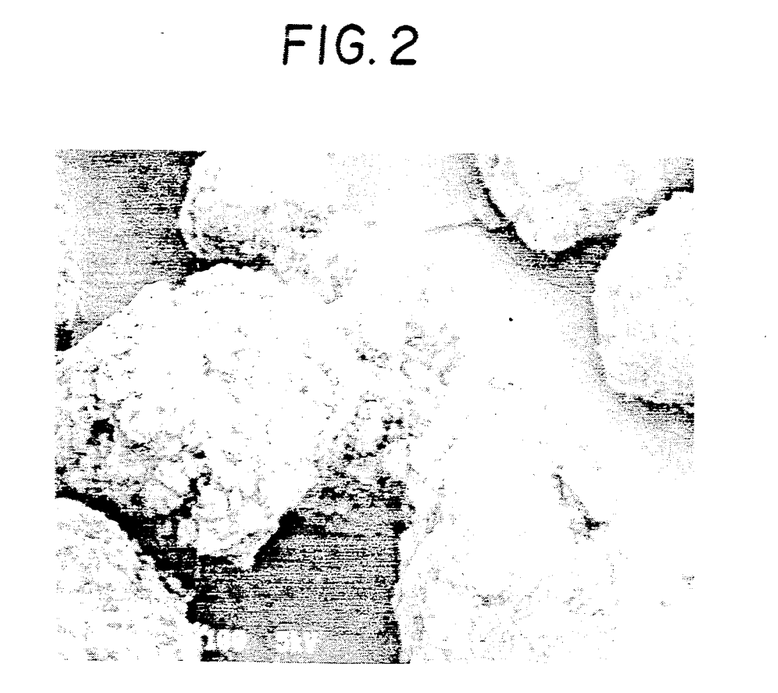
FIG. 2 is an electron micrograph of Example 4, Inventive Run 2 at 100X.

The inventive inclusion complex when viewed under an electron microscope at both 50X and 100X shows the granulate to be a round particle, which is smooth having no apparent fractures. See FIGS. 1 and 2.

EXAMPLE 2

Comparative Run A

Preparation of Choline Magnesium Trisalicylate

This example illustrates the preparation of a non-stable, solid choline magnesium salicylate composition by a granulation technique employing liquid choline salicylate.

The following components are utilized in the composition:

| Ingredient | Weight Percent |
|---|---|
| Choline Salicylate (80%) | 34.6 |
| Magnesium Salicylate | 42.8 |
| Silicon Dioxide | 16.4 |
| Sodium Starch Glycolate | 4.0 |
| Talc | 1.1 |
| Magnesium Stearate | 1.1 |
| | 100.0 |

The magnesium salicylate, silicon dioxide and about 60.0% of the sodium starch glycolate are placed into a mixer and blended for fifteen minutes. After a homogeneous mixture is obtained, the blend is granulated with liquid choline salicylate. The resulting wet mass is then transferred onto paper-lined trays and dried in a tray drier at 40° C. to 50° C. for not less than about 12 hours. The dried mass is milled through a #12 mesh screen. Upon checking the amount of weight lost from drying, the mass is redried until the total weight is within the desired range. The dried mass, talc (screened through a #18 mesh screen), and the remainder of the sodium starch glycolate are then transferred into a blender and blended for about 15 minutes.

The blend is recycled and blended for 10 more minutes. The magnesium stearate is screened through a #18 mesh screen directly into the blender and the mixture is blended for an additional 5 minutes.

The resulting dry choline magnesium salicylate composition shows heavy sticking when compressed into tablet form. The composition is found to be unstable and highly hygroscopic (deliquescent) in the presence of moisture.

EXAMPLE 3

Comparative Run B

The procedure of Experiment 1 of U.S. Pat. No. 3,759,980 was repeated as follows:

17.02 grams of 90% choline salicylate, 18.84 grams of magnesium salicylate tetrahydrate, and 12.00 milliliters water were mixed in a warmed steam bath to give a clear yellow solution. The water was then removed by drying at reduced pressure and elevated temperature to yield a white solid having the following composition.

| | | |
|---|---|---|
| A. 20-23% | CHOLINE | |
| B. 3-4.5% | MAGNESIUM | |
| C. 70-74% | SALICYLATE | |
| D. 2-4% | WATER | |
| MOLAR PROPORTION: | 5:4:13:3 | |
| WEIGHT RATIO BASIS: | CHOLINE | 1-30% |
| | MAGNESIUM | 2-15% |
| | SALICYLATE | 60-90% |

Moisture content of the solid was checked initially and found to be 3.03%. When the formulation was subjected to ambient and high humidity conditions and checked by the Karl-Fisher method, the formulation was determined to be completely non-deliquescent. See Table I. In contrast, when the formulation of Example 4 Inventive Run 2 was tested under identical conditions, the Inventive Run 2 formulation was found to be hygroscopic. The results are also set forth in Table I.

Figure 3:
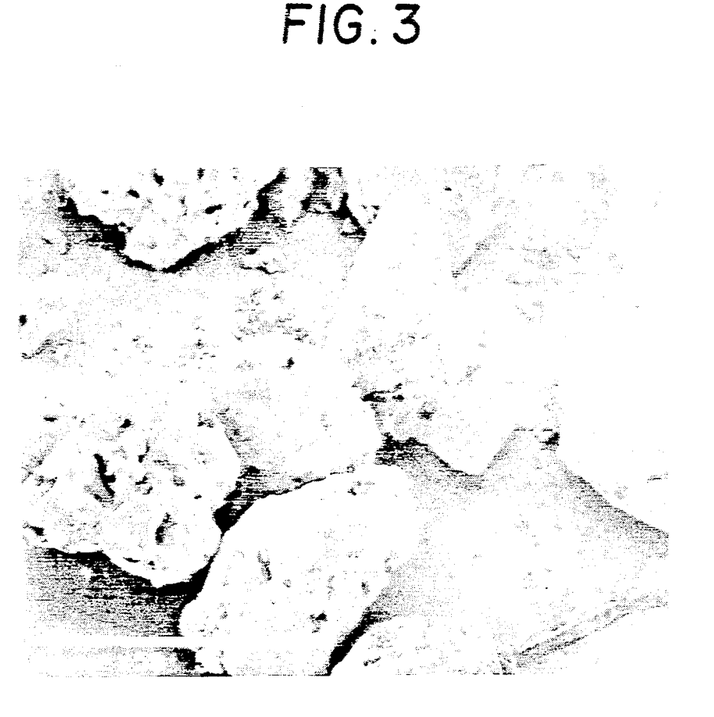
FIG. 3 is an electron micrograph of Example 3, Comparative Run B at 50X.
Figure 4:
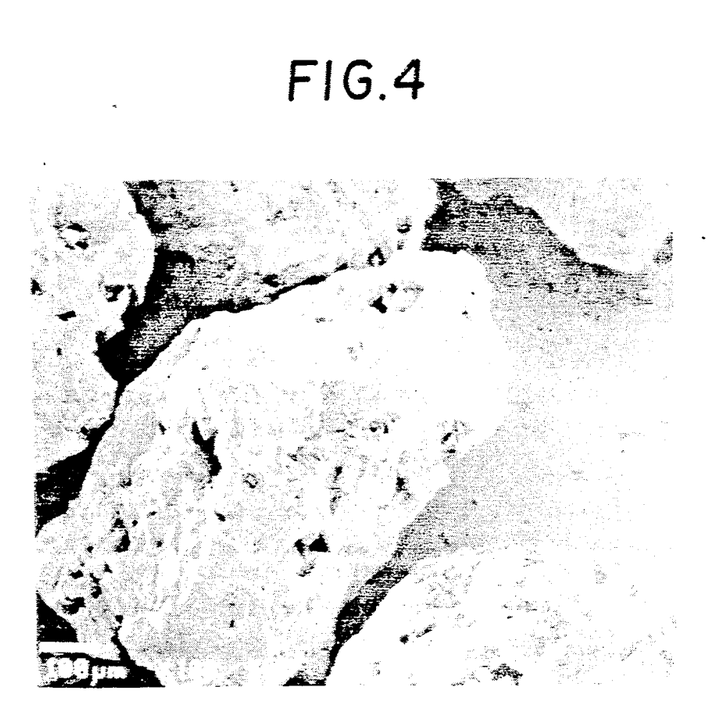
FIG. 4 is an electron micrograph of Example 3, Comparative Run B at 100X.

When the Rosen et al. complex was ground and passed through a #18 mesh screen, U.S. standard sieve and viewed under an electron microscope at both 50X and 100X the complex has the appearance of broken glass which has an irregular structure, sharp edges and clear fracture points. See FIGS. 3 and 4.

EXAMPLE 4

Inventive Runs 2 and 3; Comparative Runs C to E

This Example demonstrates the formation of an inclusion complex by the inventive formulation and differentiates this complex from the complex of Rosen et al. set forth in Example 3, Comparative Run B.

In Inventive Run 2, the inclusion complex of the invention was prepared containing the following components:

| | |
|---|---|
| choline salicylate (80%) | 183.1 grams |
| magnesium salicylate (85%) | 212.9 grams |
| magnesium aluminum silicate | 47.0 grams |
| fumed silicon dioxide | 59.5 grams |
| sodium starch glycolate | 11.0 grams |
| | 513.5 grams |

The inclusion complex was prepared by screening the four powders through #18 mesh U.S. standard sieve and granulating the powders with liquid choline salicylate by mixing for 15 minutes. The granules were tray dried at 40°-50° C. and screened through a #12 mesh, U.S. standard sieve. The moisture of the product was then tested by Karl-Fischer method was 5.34%.

The Inventive Run 3, the method of Inventive Run 2 was repeated for making an inclusion complex not containing sodium starch glycolate. In this example, however, the granulate was screened through a #18 mesh screen, U.S. standard sieve. The composition contained the following components:

| | |
|---|---|
| choline salicylate (80%) | 18.31 grams |
| magnesium salicylate (85%) | 21.29 grams |
| magnesium aluminum silicate | 4.70 grams |
| fumed silicon dioxide | 5.95 grams |
| | 50.25 grams |

In Comparative Runs C and D, the Rosen et al. composition of Example 3 was ground and passed through a #18 mesh screen, U.S. standard sieve. To this comparative complex was dry blended powdered magnesium aluminum silicate in Run C and additionally fumed silicon dioxide in Run D. The formulations contained the following components:

| Ingredients | Run C | Run D |
|---|---|---|
| Rosen choline magnesium salicylate complex | 3.342 grams | 3.342 grams |
| Magnesium aluminum silicate | 0.47 grams | 0.47 grams |
| Fumed silicon dioxide | — | 0.595 grams |
| | 3.812 grams | 4.407 grams |

In Comparative Run E, the Rosen et al. complex of Example 3 was ground and passed through a #18 mesh screen, U.S. standard sieve. To this material was dry blended a powdered mixture, containing three components as follows:

| | |
|---|---|
| Rosen choline magnesium salicylate complex | 10.026 grams |
| magnesium aluminum silicate | 1.41 grams |
| fumed silicon dioxide | 1.785 grams |
| sodium starch glycolate | 0.330 grams |
| | 13.551 grams |

Figure 5:
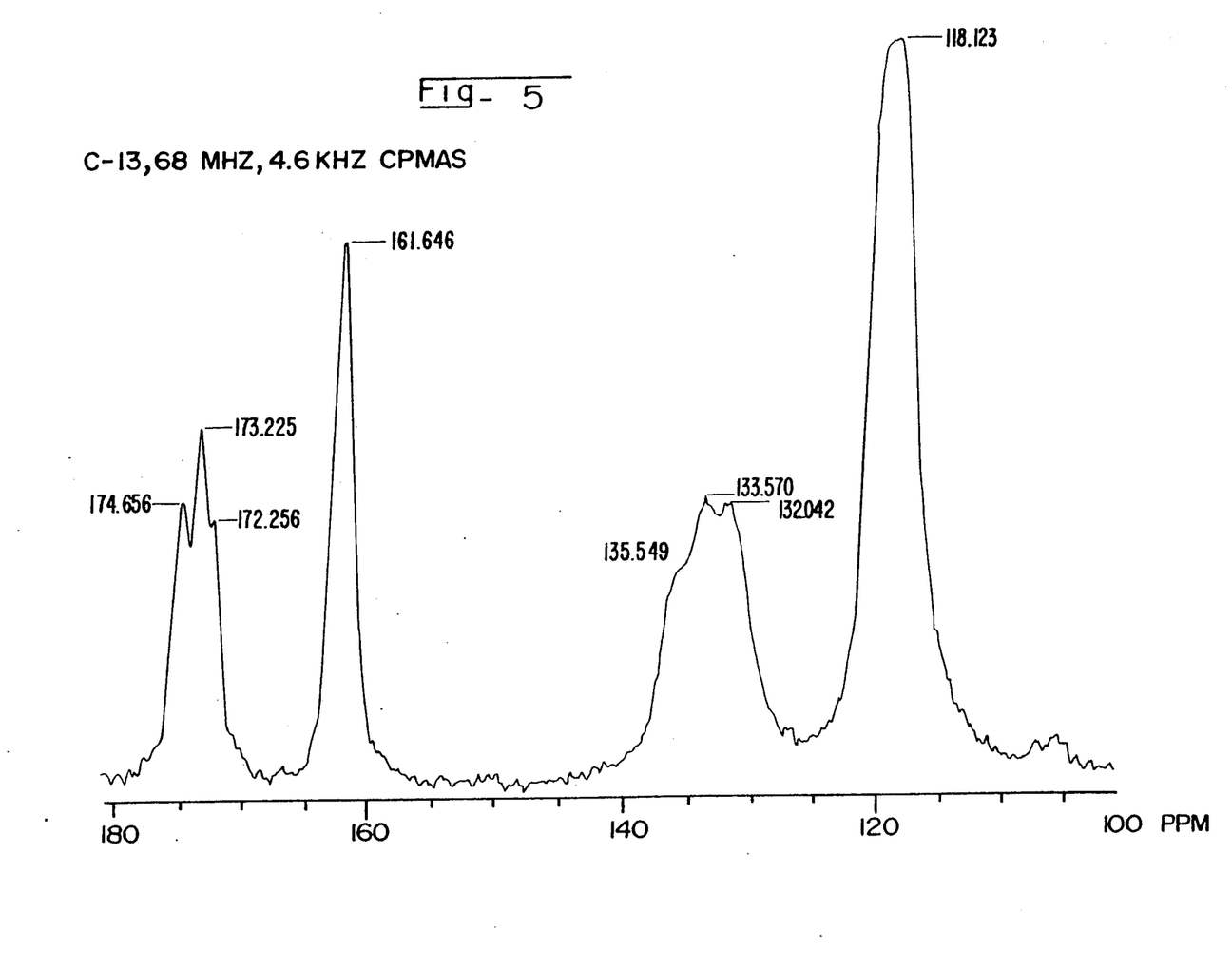
FIG. 5 is an NMR pattern for the inventive inclusion complex.

All samples were analyzed using NMR (nuclear magnetic resonance) under the same conditions. The graphs depicting the relevant frequencies are set forth in FIGS. 5 to 10. The formulations presented are as follows:

FIG. 5. Composition prepared according to Inventive Run 2.

Figure 6:
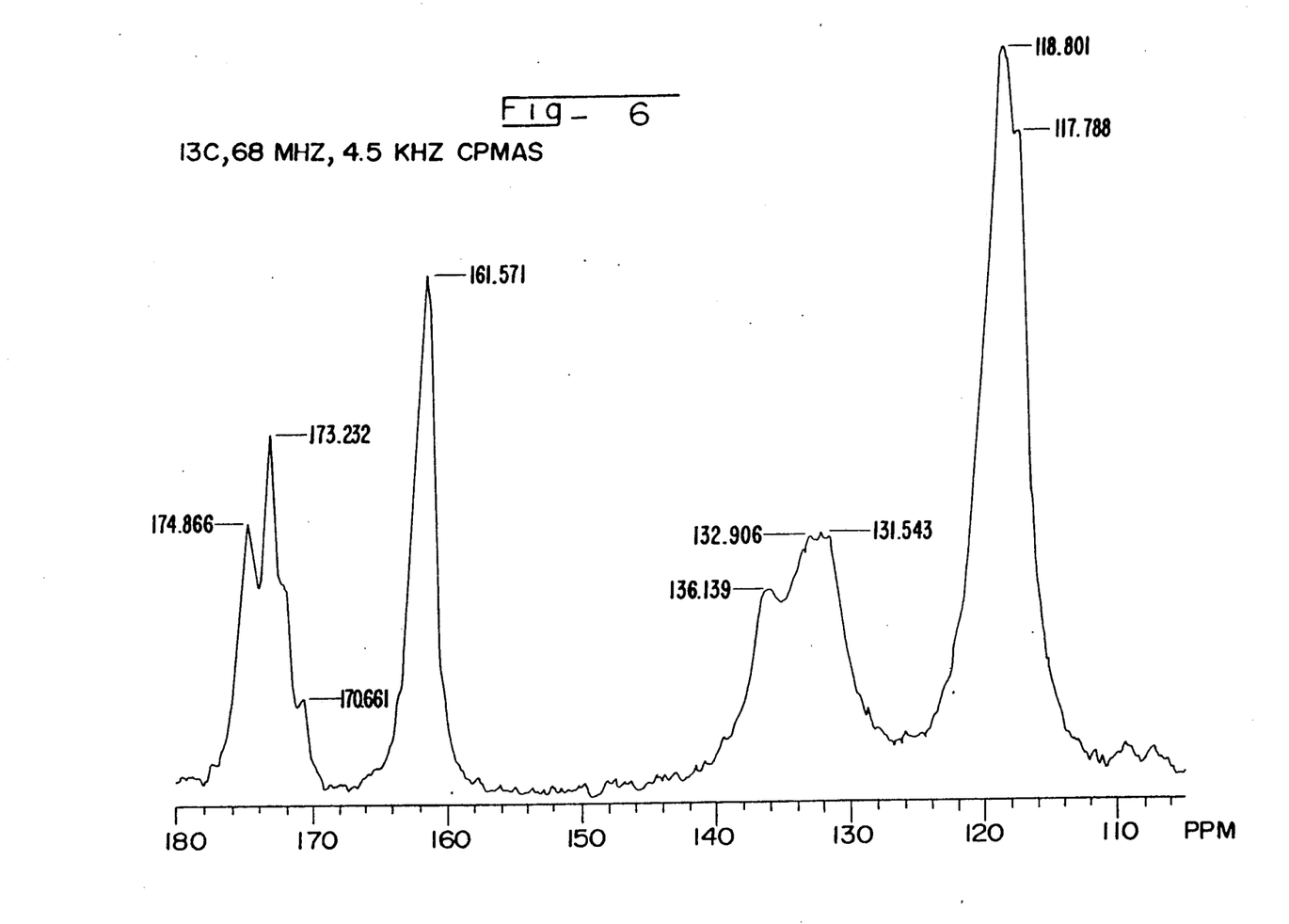
FIG. 6 is an NMR pattern for the inventive inclusion complex.

FIG. 6. Composition prepared according to Inventive Run 3 without sodium starch glycolate, Inventive Run 3.

Figure 7:
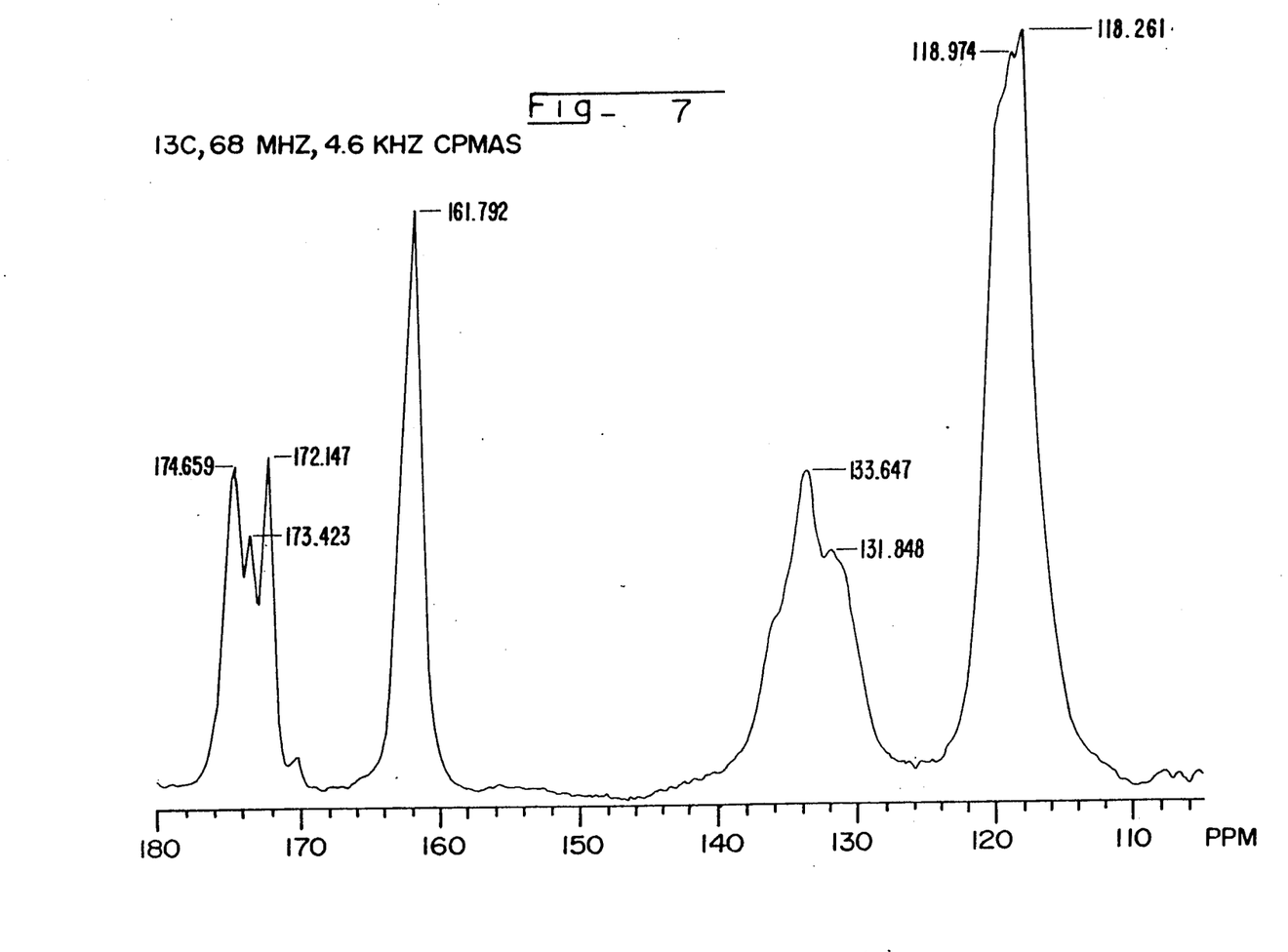
FIG. 7 is an NMR pattern for a comparative complex.

FIG. 7. Rosen complex prepared according to Comparative Run B.

Figure 8:
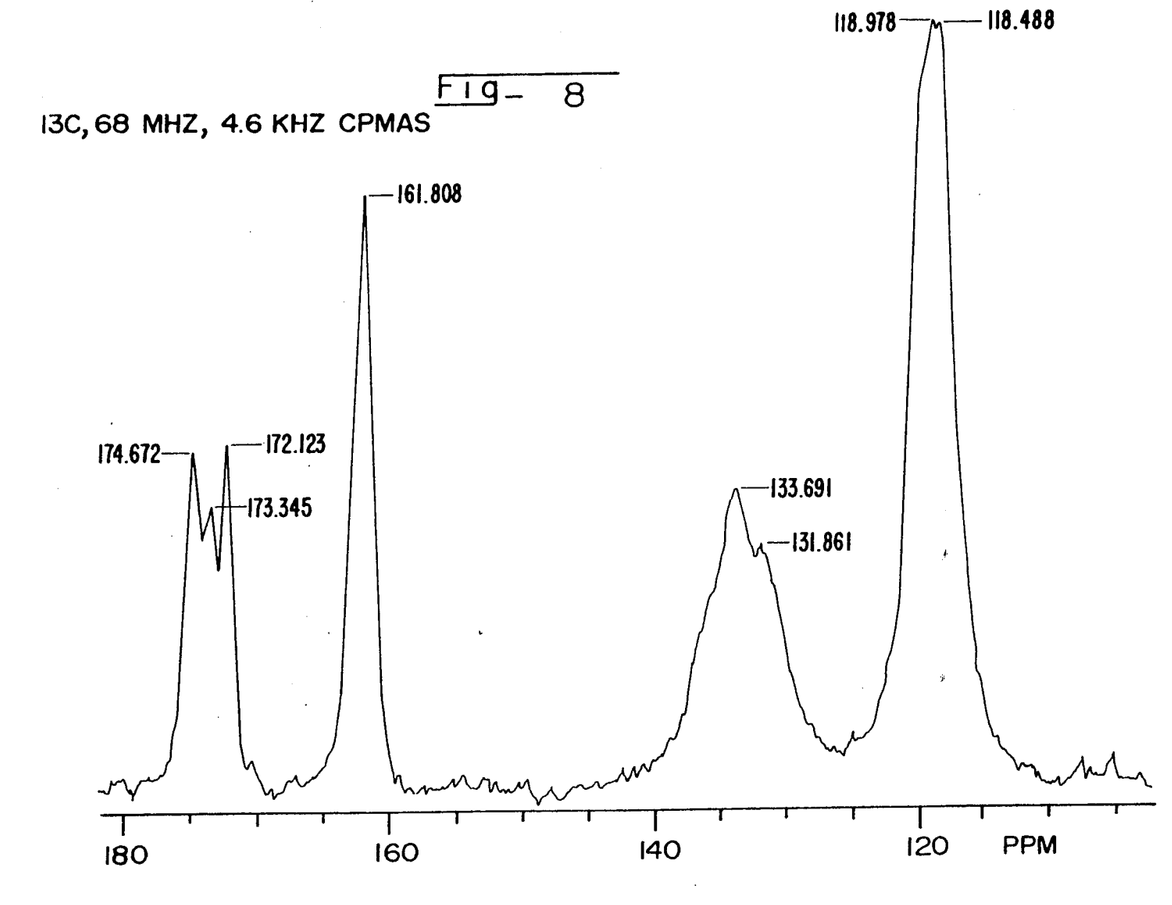
FIG. 8 is an NMR pattern for a comparative complex with powdered magnesium aluminum silicate.

FIG. 8. Rosen complex prepared according to Comparative Run C.

Figure 9:
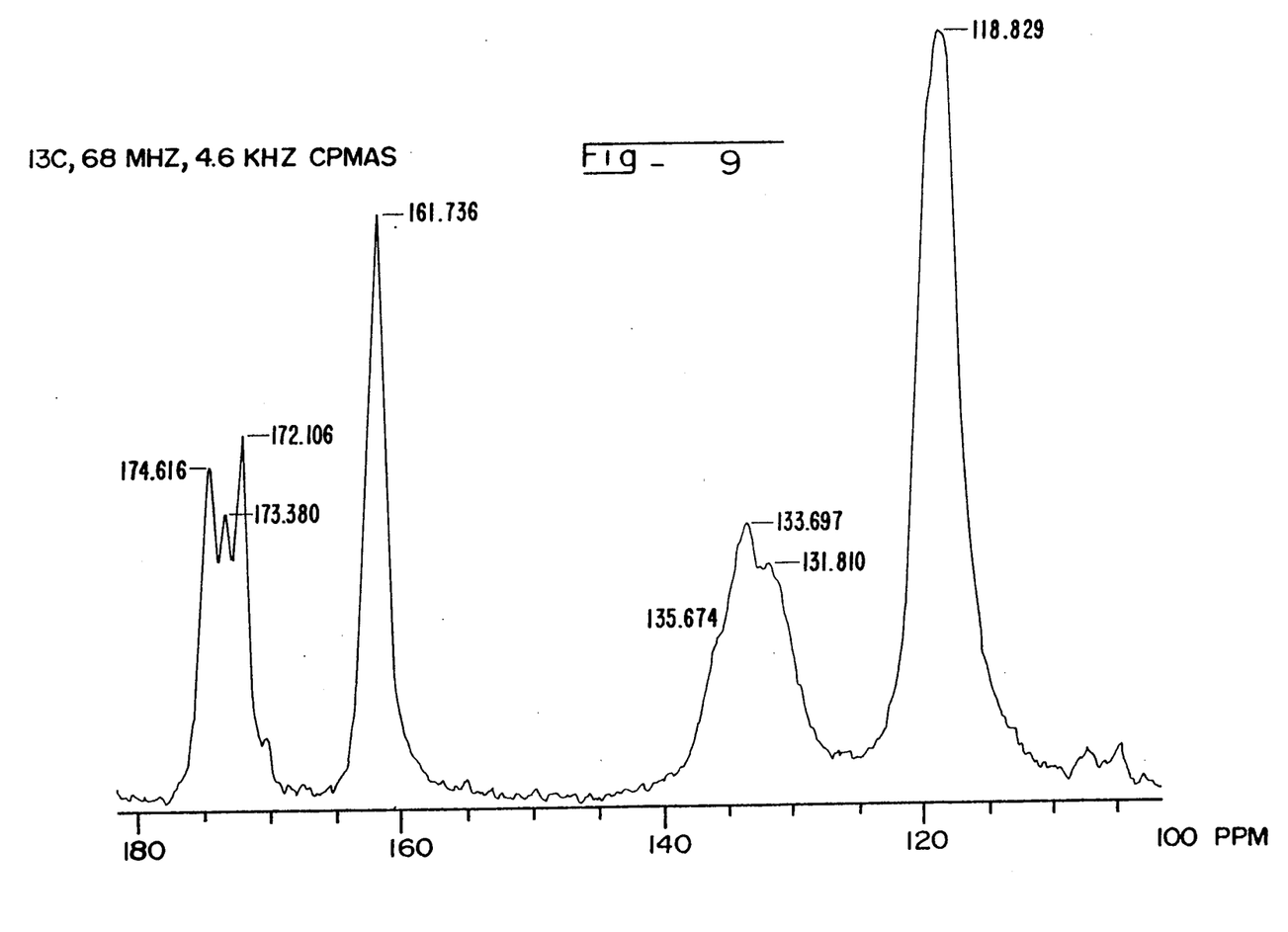
FIG. 9 is an NMR pattern for a comparative complex with powdered magnesium aluminum silicate and silicon dioxide.

FIG. 9. Rosen complex prepared according to Comparative Run D.

Figure 10:
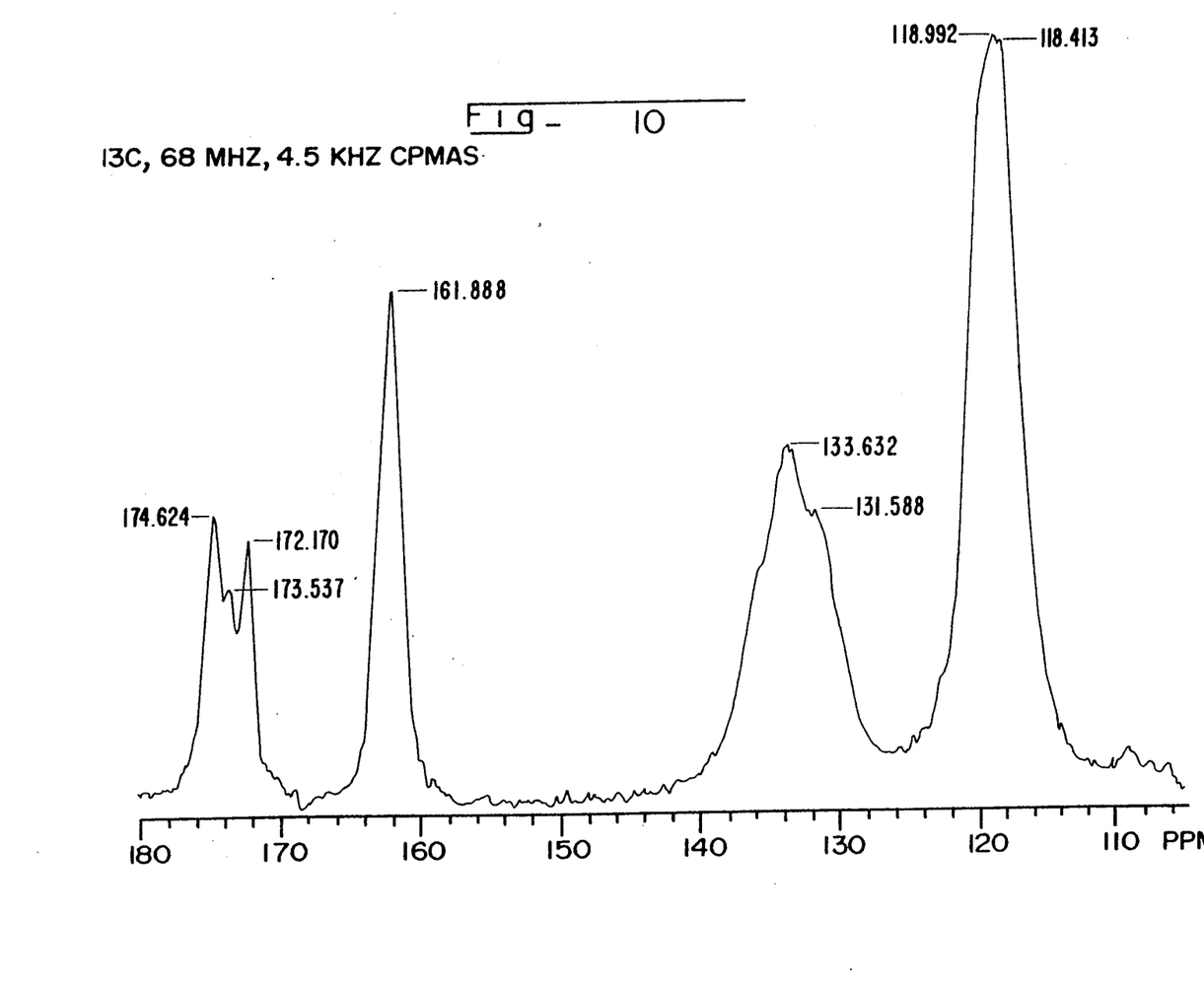
FIG. 10 is an NMR pattern for a comparative complex with powdered magnesium aluminum silicate, silicon dioxide and sodium starch glycolate.

FIG. 10. Rosen complex prepared according to Comparative Run E.

The results indicate that the Rosen complex, whether tested alone or as a dry mixture with powdered magnesium aluminum silicate, alone or with silicon dioxide, and again in combination with the foregoing or additionally with sodium starch glycolate, all exhibited virtually identical bonding patterns. This result indicates that the presence of the added powdered components did not modify the bonding frequencies of the Rosen et al. complex.

In contrast to these results, the formulations depicted in Inventive FIGS. 5 and 6 show modified bonding frequencies at the carbonyl and aromatic frequency ranges over the Rosen et al. complex. This modified pattern clearly indicates the formation of an inclusion complex resulting from the presence of the magnesium aluminum silicate with virtually no effect being evident from the sodium starch glycolate.

The invention being thus described, it will be obvious that the same may be varied in many ways. Such variations are not to be regarded as a departure from the spirit and scope of the invention and all such modifications are intended to be included within the scope of the following claims.

TABLE I

WATER DETERMINATION BY KARL FISCHER METHOD

| Comparative Run B Water | | | Inventive Run 2 Water | | |
|---|---|---|---|---|---|
| Condition | Initial | 3.03% | Condition | Initial | 5.34% |
| Ambient | 4th Hour | 2.57% | Ambient | 4th Hour | 6.06% |
| Ambient | 7th Hour | 2.38% | Ambient | 7th Hour | 5.61% |
| Ambient | 24th Hour | 2.88% | Ambient | 24th Hour | 7.18% |
| 75% RH | 24th Hour | 3.33% | 75% RH | 24th Hour | 8.55% |

RH means Relative Humidity
Ambient conditions possessed about 45% moisture.

What is claimed is:

1. A stable, solid choline magnesium salicylate inclusion complex composition, which comprises: choline salicylate, magnesium salicylate and magnesium aluminum silicate.

2. The composition of claim 1, wherein the molar ratio of salicylate anion to choline cation and magnesium cation is about 7.2 to 2.4 and 6.0.

3. The composition of claim 1, wherein the choline salicylate and magnesium salicylate are present in the amount of about 65% to about 85% by weight of the entire composition.

4. The composition of claim 3, wherein the choline salicylate is present in amounts of about 25% to about 45% by weight, and the magnesium salicylate is present in an amount of about 25% to about 45% by weight of the total composition.

5. The composition of claim 1, wherein the magnesium aluminum silicate is present in an amount of about 6% to about 35% by weight of the total composition.

6. The composition of claim 1, further including a pharmaceutically acceptable agent selected from the group consisting of fillers, extenders, colorants, flavorants, non-reactive buffers, preservatives, tableting excipients and mixtures thereof.

7. The composition of claim 6, wherein the pharmaceutically acceptable agent is selected from the group consisting of silicon dioxide, sodium starch glycolate and mixtures thereof.

8. The composition of claim 7, wherein the silicon dioxide is present in an amount of about 6% to about 35% by weight of the total composition.

9. The composition of claim 1 wherein the composition contains silicon dioxide and wherein the combined amount of magnesium aluminum silicate and silicon dioxide is from about 15% to about 35% by weight of the total composition.

10. The composition of claim 9 wherein the composition has a percent weight ratio of magnesium aluminum silicate to silicon dioxide of 70:30 to 30:70.

11. The composition of claim 5, wherein the magnesium aluminum silicate is present in an amount of about 8% to about 15% by weight of the total composition.

12. The composition of claim 8, wherein the silicon dioxide is present in an amount of about 8% to about 15% by weight of the total composition.

13. The composition of claim 1, further including sorbed water.

14. The composition of claim 13 wherein the water is present in an amount of about 3.5% to about 10% by weight of the total composition.

15. The composition of claim 14, further including a pharmaceutically acceptable agent selected from the group consisting of fillers, extenders, colorants, flavorants, non-reactive buffers, preservatives, tableting excipients and mixtures thereof.

16. The composition of claim 15, wherein the pharmaceutically acceptable agent is selected from the group consisting of silicon dioxide, sodium starch glycolate and mixtures thereof.

17. The composition of claim 1 which is in the form of a tablet, capsule, granule or suppository.

18. A process for preparing a stable, solid choline magnesium salicylate inclusion complex composition, which comprises:
   (a) providing a dry mixture comprising magnesium salicylate and magnesium aluminum silicate;
   (b) granulating said mixture with liquid choline salicylate to form a solid choline magnesium salicylate inclusion complex containing magnesium aluminum silicate; and
   (c) recovering the product as a stable, solid choline magnesium salicylate inclusion complex.

19. The process of claim 18, wherein the magnesium salicylate and magnesium aluminum silicate are mixed as solid free-flowing powders.

20. The process of claim 18, wherein the mixture of step (a) further includes a pharmaceutically acceptable agent selected from the group consisting of silicon dioxide, sodium starch glycolate, and mixtures thereof.

21. The process of claim 18, wherein the mixture of step (a) is mixed to provide a homogeneous mixture prior to granulating in step (b).

22. The process of claim 18, wherein the granulated mixture of step (b) is dried at a temperature of from about 28° C. to about 60° C. for not less than about 12 hours.

23. The process of claim 22, wherein the drying step is performed at a temperature of about 40° C. to about 50° C.

24. The process of claim 18 wherein the choline salicylate and magnesium salicylate are employed in the process in an amount of about 65% to about 85% by weight of the total composition.

25. The process of claim 18, wherein the magnesium aluminum silicate is present in an amount of about 6% to about 35% by weight of the total composition.

26. The process of claim 20 wherein the silicon dioxide is present in an amount of about 6% to about 35% by weight of the total composition.

27. The process of claim 18, wherein the mixture of step (a) additionally contains silicon dioxide and wherein the combined amount of magnesium aluminum silicate and silicon dioxide is from about 15% to about 35% of the total composition.

28. The process of claim 27 wherein the composition has a percent weight ratio of magnesium aluminum silicate to silicon dioxide of 70:30 to 30:70.

29. The process of claim 18 wherein the magnesium aluminum silicate is present in an amount of about 8% to about 15% by weight of the total composition.

30. The process of claim 26, wherein the silicon dioxide is present in an amount of about 8% to about 15% by weight of the total composition.

31. The process of claim 18, wherein the inclusion complex additionally contains water.

32. The process of claim 31 wherein the water is present in an amount of about 3.5% to about 10% by weight of the entire composition.

33. The process of claim 18, wherein the liquid choline salicylate is added to powdered free-flowing magnesium salicylate and magnesium aluminum silicate and admixed to form the granulated product.

34. The process of claim 18, wherein powdered magnesium salicylate and magnesium aluminum silicate are added to the liquid choline salicylate and admixed to form the granulated product.

35. The process of claim 18, wherein the liquid choline salicylate contains about 5% to about 85% choline salicylate and remainder water by weight.

36. The process of claim 33, wherein the liquid choline salicylate is slowly added to the powdered mixture while mixing to form the granulated product.

37. The process of claim 34, wherein the powders are added incrementally to the liquid choline salicylate, while the components are mixed to form the granulated product.

38. A method of treating osteoarthritis, which comprises: administering to a mammal a therapeutically effective amount of a solid choline magnesium salicylate inclusion complex according to claim 1.

39. A method of treating rheumatoid arthritis, which comprises: administering to a mammal a therapeutically effective amount of a solid choline magnesium salicylate inclusion complex according to claim 1.

40. A method of treating acute painful shoulder, which comprises: administering to a mammal a therapeutically effective amount of a solid choline magnesium salicylate inclusion complex according to claim 1.

41. A method of administering a solid choline magnesium salicylate pharmaceutical preparation to a mammal, which comprises: providing a solid choline magnesium salicylate inclusion complex comprising choline salicylate, magnesium salicylate and magnesium aluminum silicate; incorporating said solid choline magnesium salicylate inclusion complex into a pharmaceutically acceptable carrier to form a solid choline magnesium salicylate pharmaceutical preparation; and delivering said solid choline magnesium salicylate pharmaceutical preparation to the mammal.

42. The method of claim 40, wherein said pharmaceutically acceptable carrier comprises a tablet.

43. The method of claim 40, wherein said pharmaceutically acceptable carrier comprises a capsule.

44. The method of claim 40, wherein said pharmaceutically acceptable carrier comprises a granule.

45. The method of claim 40, wherein said pharmaceutically acceptable carrier comprises a suppository.

46. A pharmaceutical preparation which comprises: an effective amount of a stable, solid choline magnesium salicylate inclusion complex containing magnesium aluminum silicate and a pharmaceutically acceptable carrier.

* * * * *

UNITED STATES PATENT AND TRADEMARK OFFICE
CERTIFICATE OF CORRECTION

PATENT NO. : 5,043,168
DATED : August 27, 1991
INVENTOR(S) : S. PATEL et al.

Page 1 of 2

It is certified that error appears in the above-indentified patent and that said Letters Patent is hereby corrected as shown below:

On the title page, item [56]. U.S. Patent Documents, line 16, at end of line insert ---514/916---.

On the title page, item [56], U.S. Patent Documents, line 17, after this line insert ---3,855,282 12/1978 Kelly 514/473---.

On the title page, item [56], U.S. Patent Documents, line 19, after "Kelly" delete "et al."

On the title page, item [56]. U.S. Patent Documents, line 19, at end of line insert ---362/477---.

On the title page, item [56]. U.S. Patent Documents, line 20, at end of line insert ---514/63---.

On the title page, item [56]. U.S. Patent Documents, line 21, after "Kelly" delete "et al."

On the title page, item [56]. U.S. Patent Documents, line 21, at end of line insert ---362/477---.

UNITED STATES PATENT AND TRADEMARK OFFICE
CERTIFICATE OF CORRECTION

PATENT NO. : 5,043,168
DATED : August 27, 1991
INVENTOR(S) : S. PATEL et al.

It is certified that error appears in the above-indentified patent and that said Letters Patent is hereby corrected as shown below:

On the title page, item [56],
U.S. Patent Documents, line 22, at end of line insert ---514/160---.

On the title page, item [56],
U.S. Patent Documents, line 22, below this line insert ---4,680,309 7/1987 Maura et al. 514/499---.

On the title page, item [56],
U.S. Patent Documents, line 24, below this line insert ---4,287,174 9/1981 Laughlin 514/927---.

On the title page, item [56],
U.S. Patent Documents, line 26, below this line insert ---4,867,979 9/1982 Sirri et al. 514/188---.

On the title page, item [56],
Foreign Patent Documents, line 1, below this line insert ---2701553 7/1977 Germany---.

Signed and Sealed this

Nineteenth Day of November, 1996

Attest:

BRUCE LEHMAN

Attesting Officer        Commissioner of Patents and Trademarks